United States Patent
Prisco et al.

(10) Patent No.: US 9,566,124 B2
(45) Date of Patent: *Feb. 14, 2017

(54) METHODS FOR HANDLING AN OPERATOR COMMAND EXCEEDING A MEDICAL DEVICE STATE LIMITATION IN A MEDICAL ROBOTIC SYSTEM

(71) Applicant: INTUITIVE SURGICAL OPERATIONS INC., Sunnyvale, CA (US)

(72) Inventors: Giuseppe Maria Prisco, Calci (IT); David J. Rosa, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/970,942

(22) Filed: Dec. 16, 2015

(65) Prior Publication Data

US 2016/0166344 A1   Jun. 16, 2016

Related U.S. Application Data

(62) Division of application No. 11/613,926, filed on Dec. 20, 2006, now Pat. No. 9,241,767.

(Continued)

(51) Int. Cl.
*B25J 3/04* (2006.01)
*B25J 9/16* (2006.01)
*A61B 17/00* (2006.01)

(52) U.S. Cl.
CPC .............. *A61B 34/37* (2016.02); *A61B 34/35* (2016.02); *A61B 34/70* (2016.02); *B25J 3/04* (2013.01);

(Continued)

(58) Field of Classification Search
CPC ....... G06F 3/016; G06F 3/0481; G06F 9/4443
See application file for complete search history.

(56) References Cited

U.S. PATENT DOCUMENTS

| 4,772,831 A | 9/1988 | Casler, Jr. et al. |
| 4,851,748 A | 7/1989 | Daggett et al. |

(Continued)

FOREIGN PATENT DOCUMENTS

WO    WO-2005098556 A2    10/2005

OTHER PUBLICATIONS

Bartolini Giorgio et al., "Hybrid Second Order Sliding Mode Control of Constrained Manipulators with Frictional Contact," Proceedings of the 40th IEEE Conference on Decision and Control, 2001, pp. 1398-1403, vol. 2, IEEE.

(Continued)

*Primary Examiner* — Gary Jackson
*Assistant Examiner* — Jeffrey Lipitz

(57) ABSTRACT

A medical robotic system has a robotic arm holding a medical device, and a control system for controlling movement of the arm according to operator manipulation of an input device. If the medical device is being commanded to a state exceeding a limitation by a threshold amount, then the control system disengages control of the medical device by the input device, servos the arm so that it remains in its current state, servos the input device so that it is set at a position such that a force being applied on the input device remains at its current level, requests the operator to lighten hold of the input device, sets a parameter associated with the input device upon detecting such lightened hold so that the medical device is commanded to a different state that does not exceed the limitation, and reengages control of the medical device by the input device.

20 Claims, 4 Drawing Sheets

Related U.S. Application Data

(60) Provisional application No. 60/752,174, filed on Dec. 20, 2005.

(52) U.S. Cl.
CPC .............. *B25J 9/1674* (2013.01); *B25J 9/1689* (2013.01); *A61B 34/30* (2016.02); *A61B 90/361* (2016.02); *A61B 2017/00115* (2013.01); *A61B 2017/00119* (2013.01); *A61B 2017/00123* (2013.01); *A61B 2034/305* (2016.02); *A61B 2090/065* (2016.02)

(56) References Cited

U.S. PATENT DOCUMENTS

| | | | |
|---|---|---|---|
| 4,908,556 | A | 3/1990 | Daggett et al. |
| 4,925,312 | A | 5/1990 | Onaga et al. |
| 5,049,796 | A | 9/1991 | Seraji |
| 5,231,693 | A | 7/1993 | Backes et al. |
| 5,285,379 | A | 2/1994 | Gamble |
| 5,371,669 | A | 12/1994 | Venkataraman et al. |
| 5,377,106 | A | 12/1994 | Drunk et al. |
| 5,389,865 | A | 2/1995 | Jacobus et al. |
| 5,408,409 | A | 4/1995 | Glassman et al. |
| 5,762,458 | A | 6/1998 | Wang et al. |
| 5,993,338 | A | 11/1999 | Kato et al. |
| 6,424,885 | B1 | 7/2002 | Niemeyer et al. |
| 6,459,926 | B1 | 10/2002 | Nowlin et al. |
| 6,507,997 | B2 | 1/2003 | Tsuchiya et al. |
| 6,516,235 | B1 | 2/2003 | Kono et al. |
| 6,587,750 | B2 | 7/2003 | Gerbi et al. |
| 6,671,581 | B2 | 12/2003 | Niemeyer et al. |
| 6,798,611 | B1 | 9/2004 | Romano et al. |
| 6,839,612 | B2 | 1/2005 | Sanchez et al. |
| 6,879,880 | B2 | 4/2005 | Nowlin et al. |
| 6,963,792 | B1 | 11/2005 | Green |
| 7,087,049 | B2 | 8/2006 | Nowlin et al. |
| 7,453,227 | B2 | 11/2008 | Prisco et al. |
| 7,741,802 | B2 | 6/2010 | Prisco et al. |
| 7,899,578 | B2 | 3/2011 | Prisco et al. |
| 2001/0000663 | A1 | 5/2001 | Shahoian et al. |
| 2002/0042620 | A1 | 4/2002 | Julian et al. |
| 2002/0120363 | A1 | 8/2002 | Salisbury et al. |
| 2003/0216715 | A1 | 11/2003 | Moll et al. |
| 2003/0216836 | A1 | 11/2003 | Treat et al. |
| 2004/0034302 | A1 | 2/2004 | Abovitz et al. |
| 2005/0024331 | A1 | 2/2005 | Berkley et al. |
| 2007/0142825 | A1 | 6/2007 | Prisco et al. |
| 2007/0167702 | A1 | 7/2007 | Hasser et al. |
| 2011/0160904 | A1 | 6/2011 | Prisco et al. |
| 2011/0166706 | A1 | 7/2011 | Prisco et al. |

OTHER PUBLICATIONS

Bhat, Sanjay P. et al., "Continuous Finite—Time Stabilization of the Translational and Rotational Double Integrators," IEEE Transactions on Automatic Control, 1998, IEEE Transactions on Automatic Control, pp. 678-682, vol. 43, No. 5, IEEE.

Buttolo, Pietro et al., "Sliding Control of Force Reflecting Teleoperation: Preliminary Studies," Presence, 1994, pp. 158-172, vol. 3—No. 2.

Fiene, Jonathan et al., "Toward High-Speed Switching Motor Control for Human-Interactive Robotics," Proceedings of the 2005 IEEE International Conference on Robotics and Automation, 2005, pp. 1489-1494, IEEE.

Fridman, L., "The Problem of Chattering: an Averaging Approach," Lecture Notes in Control and Information Sciences, vol. 247, pp. 363-392, 1999, Springer Verlag, Berlin/Heidelberg.

Golo, Goran et al., "Robust discrete-time chattering free sliding mode control," Systems and Control Letters, 2000, pp. 19-28, vol. 41, No. 1, Elsevier.

Guldner, J. et al., "The chattering problem in sliding mode systems," 12th International Symposium on Mathematical Theory of Networks and Systems, 2000, Perpignan, France, 8 pages.

Hung, John Y. et al, "Variable Structure Control: A Survey," IEEE Transactions on Industrial Electronics, 1993, pp. 2-22, vol. 40 No. 1, IEEE.

Iliev B., et al., "Minimum-time Sliding Mode Control for Second-order Systems," Proceeding of the 2004 American Control Conference Boston, Massachusetts Jun. 30-Jul. 2, 2004, WeA19.3, pp. 626-631.

Jezernik, Karel et al., "Observer Based Sliding Mode Control of Robotic Manipulator," Robotica, vol. 12, 1994, pp. 1-14.

Kikuuwe, Ryo et al., "Proxy-Based Sliding Mode Control for Accurate and Safe Position Control," IEEE International Conference on Robotics and Automation, 2006, pp. 25-30, IEEE.

Kwon, Dong-Soo et al., "Design of a Teleoperation Controller for an Underwater Manipulator," IEEE International Conference on Robotics and Automation, 2000, pp. 3114-3119, vol. 4, IEEE.

Lee, Seok-Beom et al., "Sliding Mode Compensation of Dry Friction," Proceedings of the 1996 IEEE International Conference on Control Applications, 1996, pp. 809-813, IEEE.

Levant, Arie et al., "Robustness issues of 2-sliding mode control," IEE Control Engineering Series, Issue 66, 2004, 37 pages, Peter Peregrinus Ltd.

Monsees, Govert, "Discrete-Time Sliding Mode Control," 2002, 182 pages. Internet: http://www.dcsc.tudelft.nl/Research/PublicationFiles/publication-5390.pdf.

Monsees, Govert et al., "Adaptive Switching Gain for a Discrete-Time Sliding Mode Controller, Proceedings of the American Control Conference," 2000, pp. 1639-1643, vol. 3, IEEE.

Newman, W.S., "Robust Near Time-Optimal Control," IEEE Transactions on Automatic Control, vol. 35, No. 7, pp. 841-844, 1990, IEEE.

Nguyen, Tri V.M. et al., "A Chattering-Free Variable Structure Controller for Tracking of Robotic Manipulators," Proceedings of the 2003 Australasian Conference on Robotics & Automation, 2003, pp. 1-6.

PCT/US06/62413 International Search Report and Written Opinion of the International Searching Authority, mailed Nov. 14, 2007, 9 pages.

Sabanovic, Asif et al., "Chattering Free Sliding Modes in Robotic Manipulators Control," IEEE/RSJ International Conference on Intelligent Robots and System, 1993, vol. 2, pp. 1-23, IEEE.

Sane, Harshad S. et al., "Modified Sliding Mode Control and its Application to Electrostatically Controlled Dual-Axis Micromirrors," Proceeding of the 2004 American Control Conference, 2004, pp. 1934-1939, vol. 3, IEEE.

Shi, Jingxin et al., "Chatter Free Variable Structure Perturbation Estimator on the Torque Control of Flexible Robot Joints with Disturbance and Parametric Uncertainties," Proceedings of the 1996 IEEE IECON 22nd International Conference on Industrial Electronics, Control, and Instrumentation, 1996, pp. 238-243, vol. 1, IEEE.

Song, Gangbing et al., "A Comparative Study of Conventional Nonsmooth Time-Invariant and Smooth Time-Varying Robust Compensators," IEEE Transactions on Control Systems Technology, 1998, vol. 6, No. 4, pp. 571-576, IEEE.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Wang, Jian et al., "Positioning and Tracking Control of an X-Y Table with Sliding Mode Control," 2003, 10 pages. Internet: http://people.mech.kuleuven.be/~jwang/paper/rocond_2003.pdf.

METHODS FOR HANDLING AN OPERATOR COMMAND EXCEEDING A MEDICAL DEVICE STATE LIMITATION IN A MEDICAL ROBOTIC SYSTEM

CROSS REFERENCE TO RELATED APPLICATIONS

This application is a divisional of U.S. application Ser. No. 11/613,926 (filed Dec. 20, 2006), which claims priority to U.S. Application No. 60/752,174 (filed Dec. 20, 2005), each of which is incorporated herein by reference.

FIELD OF THE INVENTION

The present invention generally relates to medical robotic systems and in particular, to a method for handling an operator command exceeding a medical device state limitation in a medical robotic system.

BACKGROUND OF THE INVENTION

Medical robotic systems such as those used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for minimally invasive surgery using such medical robotic systems is strong and growing.

Examples of medical robotic systems include the daVinci® Surgical System and the daVinci® S™ Surgical System from Intuitive Surgical, Inc., of Sunnyvale, Calif. Each of these systems includes a surgeon's console, a patient-side cart, a high performance three-dimensional ("3-D") vision system, and Intuitive Surgical's proprietary EndoWrist™ articulating instruments, which are modeled after the human wrist so that when added to the motions of the robotic arm assembly holding the surgical instrument, they allow at least a full six degrees of freedom of motion, which is comparable to or even greater than the natural motions of open surgery.

The patient-side cart typically includes three or more robotic arm assemblies each having a slave manipulator for holding and manipulating a medical device such as a surgical instrument or image capturing device for performing and viewing a medical procedure at a surgical site within a patient. To manipulate these medical devices, the surgeon's console also includes master input devices which may be selectively associated with the slave manipulators to manipulate their respectively held medical devices.

Whenever one of the slave manipulators reaches one or more of its workspace limits, the surgeon loses control of corresponding degrees of freedom movement of the medical device being held by that slave manipulator. Thus, unless special action is taken by a master-slave control system, operator manipulation of the associated master input device does not produce the expected response for the slave manipulator and/or its held medical device. Further, the slave manipulator response in this case may prove to be not only unintuitive to the surgeon, but also unpredictable and potentially dangerous during a surgical procedure.

One approach to mitigate this problem is to provide haptic feedback back to the master input device so as to urge the surgeon away from the workspace limitation. Although highly effective, such an approach may still be improved upon to not only ensure operation within workspace limitations, but also to provide operation that does not result in unintuitive or surgically dangerous responses.

OBJECTS AND SUMMARY OF THE INVENTION

Accordingly, one object of aspects of the present invention is a method for handling an operator command that would result in a medical device exceeding one of its state limitations so as to avoid exceeding the limitation.

Another object of aspects of the present invention is a method for handling an operator command that would result in a medical device exceeding one of its state limitations so as to avoid exceeding the limitation in such a manner so as not to result in unintuitive or dangerous behavior.

Still another object of aspects of the present invention is a method for handling an operator command that would result in a medical device exceeding one of its state limitations so as to prevent a surgeon from forceably exceeding the limitation.

These and additional objects are accomplished by the various aspects of the present invention, wherein briefly stated, one aspect is a method for handling an operator command exceeding a medical device state limitation in a medical robotic system, comprising: determining whether a robotically controlled medical device is being commanded to a state that exceeds a state limitation by a threshold amount; and if the medical device is being commanded to such a state, then disengaging control of the medical device by a master input device so that the medical device remains in its current state, providing a message to an operator of the master input device to lighten the hold of the master input device, detecting the lightened hold of the master input device by the operator, and upon such detection, setting at least one parameter associated with the master input device so that the medical device is commanded to a different state that does not exceed the state limitation and reengaging the control of the medical device by the master input device.

Another aspect is a medical robotic system comprising: a robotic arm adapted with a medical device; a master input device associated with the robotic arm for operator manipulation of the medical device; and a processor configured to determine whether the medical device is being commanded to a state that exceeds a state limitation by a threshold amount in response to the operator manipulation of the master input device, and if the medical device is being commanded to such a state, then disengage control of the medical device by the master input device so that the medical device remains in its current state, provide a message to an operator of the master input device to lighten hold of the master input device, detecting the lightened hold of the master input device by the operator, and upon such detection, set at least one parameter associated with the master input device so that the medical device is commanded to a different state that does not exceed the state limitation and reengage the control of the medical device by the master input device.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
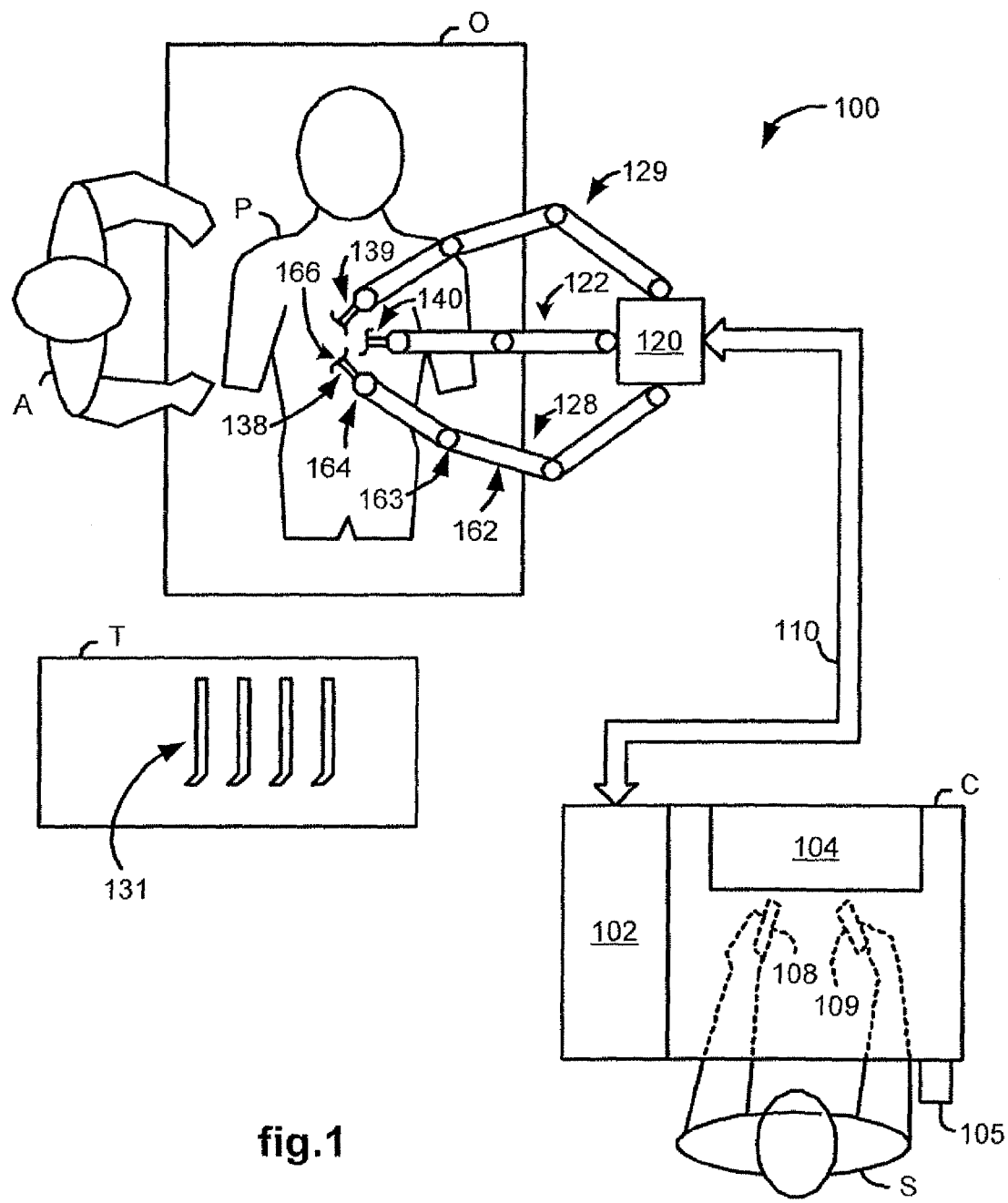
FIG. 1 illustrates a top view of an operating room employing a medical robotic system utilizing aspects of the present invention.

FIG. 1 illustrates, as an example, a top view of an operating room employing a medical robotic system. The medical robotic system in this case is a minimally invasive robotic surgical system 100 including a Console ("C") utilized by a Surgeon ("S") while performing a medical procedure, such as a diagnostic or surgical procedure, with assistance from one or more Assistants ("A"), on a Patient ("P") who is lying down on an Operating table ("O").

The Console includes a 3-D monitor 104 for displaying a 3-D image of a surgical site to the Surgeon, left and right manipulatable control devices 108, 109, a foot pedal 105, and a processor 102. The control devices 108, 109 may include any one or more of a variety of input devices such as joysticks, gloves, trigger-guns, hand-operated controllers, or the like. The processor 102 may be a dedicated computer integrated into the Console or positioned next or near to it, or it may be broken up into a number of processing or controller components that are distributed in a distributed processing fashion throughout the System 100.

The Surgeon performs a medical procedure by manipulating the input devices 108, 109 (also referred to herein as "master manipulators") so that the processor 102 causes slave manipulators of their respectively associated robotic arm assemblies 128, 129 to manipulate their respective removably coupled surgical instruments 138, 139 (also referred to herein as "tools") accordingly, while the Surgeon views the surgical site in 3-D on the Console monitor 104 as it is captured by a stereoscopic endoscope 140.

Each of the tools 138, 139, as well as the Endoscope 140, is conventionally inserted through a tool guide (not shown) into the Patient so as to extend down to the surgical site through a corresponding minimally invasive incision such as Incision 166. The number of surgical tools used at one time and consequently, the number of robotic arms being used in the system 100 will generally depend on the medical procedure being performed and the space constraints within the operating room, among other factors. If it is necessary to change a tool being used during a procedure, the Assistant may remove the tool no longer being used from its robotic arm assembly, and replace it with another tool 131 from a Tray ("T") in the operating room.

Each of the robotic arm assemblies 122, 128, 129 includes a slave manipulator and setup arms. The slave manipulators are robotically moved using motor controlled joints (also referred to herein as "active joints") in order to manipulate and/or move their respectively held medical devices. The setup arms may be manually manipulated by releasing normally braked joints (also referred to herein as "setup joints") to horizontally and vertically position the robotic arm assemblies 122, 128, 129 so that their respective medical devices may be inserted into their respective tool guides.

Preferably, the monitor 104 is positioned near the Surgeon's hands so that it will display a projected image that is oriented so that the Surgeon feels that he or she is actually looking directly down onto the operating site. To that end, images of the tools 138, 139 preferably appear to be located substantially where the Surgeon's hands are located.

The processor 102 performs various functions in the system 100. One important function that it performs is to translate and transfer the mechanical motion of control devices 108, 109 to their respective slave manipulators of robotic arm assemblies 128, 129 through control signals over bus 110 so that the Surgeon can effectively manipulate their respective tools 138, 139. Another important function is to implement various control system processes as described herein.

Although described as a processor, it is to be appreciated that the processor 102 may be implemented in practice by any combination of hardware, software and firmware. Also, its functions as described herein may be performed by one unit, or divided up among different components, each of which may be implemented in turn by any combination of hardware, software and firmware.

For additional details on the construction and operation of medical robotic systems such as described herein, see, e.g., commonly owned U.S. Pat. No. 6,493,608 "Aspects of a Control System of a Minimally Invasive Surgical Apparatus," and commonly owned U.S. Pat. No. 6,671,581 "Camera Referenced Control in a Minimally Invasive Surgical Apparatus," which are incorporated herein by reference.

Figure 2:
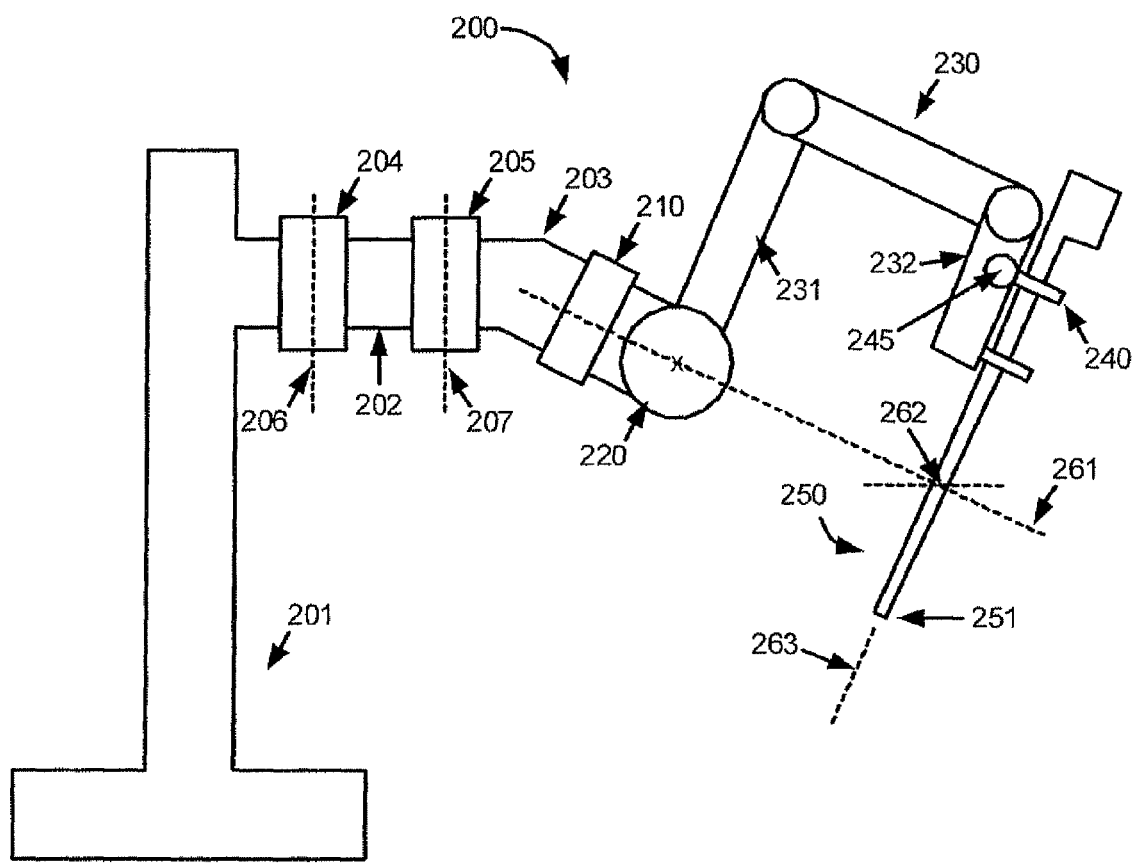
FIG. 2 illustrates a simplified side view of a robotic arm assembly employing various aspects of the present invention.

FIG. 2 illustrates, as an example, a side view of a simplified (not necessarily in proportion or complete) robotic arm assembly 200 (which is representative of the robotic arm assemblies 128, 129) holding a surgical instrument 250 (which is representative of tools 138, 139) for performing a medical procedure. The surgical instrument 250 is removably held in tool holder 240. The robotic arm assembly 200 is mechanically supported by a base 201, which may be part of a patient-side movable cart or affixed to the operating table or ceiling. It includes links 202, 203 which are coupled together and to the base 201 through horizontal setup joints 204, 205.

The setup joints 204, 205 in this example are passive joints that allow manual positioning of the arm 200 when their brakes are released. For example, setup joint 204 allows link 202 to be manually rotated about axis 206, and setup joint 205 allows link 203 to be manually rotated about axis 207. The setup arm or portion of the robotic arm assembly 200 includes these setup joints.

Although only two links and two setup joints are shown in this example, more or less of each may be used as appropriate in this and other robotic arm assemblies in conjunction with the present invention. For example, although setup joints 204, 205 are useful for horizontal positioning of the arm 200, additional setup joints may be included and useful for limited vertical and angular positioning of the arm 200. For major vertical positioning of the arm 200, however, the arm 200 may also be slidably moved along the vertical axis of the base 201 and locked in position.

The robotic arm assembly 200 also includes three active joints driven by motors. A yaw joint 210 allows arm section 230 to rotate around an axis 261, and a pitch joint 220 allows arm section 230 to rotate about an axis perpendicular to that of axis 261 and orthogonal to the plane of the drawing. The slave manipulator of the robotic arm assembly 200 includes these active joints.

The arm section 230 is configured so that sections 231, 232 are always parallel to each other as the pitch joint 220 is rotated by its motor. As a consequence, the instrument 250 may be controllably moved by driving the yaw and pitch motors so as to pivot about the pivot point 262, which is generally located through manual positioning of the setup joints 204, 205 so as to be at the point of incision into the patient. In addition, an insertion gear 245 may be coupled to a linear drive mechanism (not shown) to extend or retract the instrument 250 along its axis 263.

Although each of the yaw, pitch and insertion joints or gears, 210, 220, 245, is controlled by an individual joint or gear controller, the three controllers are controlled by a common master/slave control system so that the slave manipulator of the robotic arm assembly 200 may be controlled through user (e.g., surgeon) manipulation of its associated master manipulator.

Figure 3:
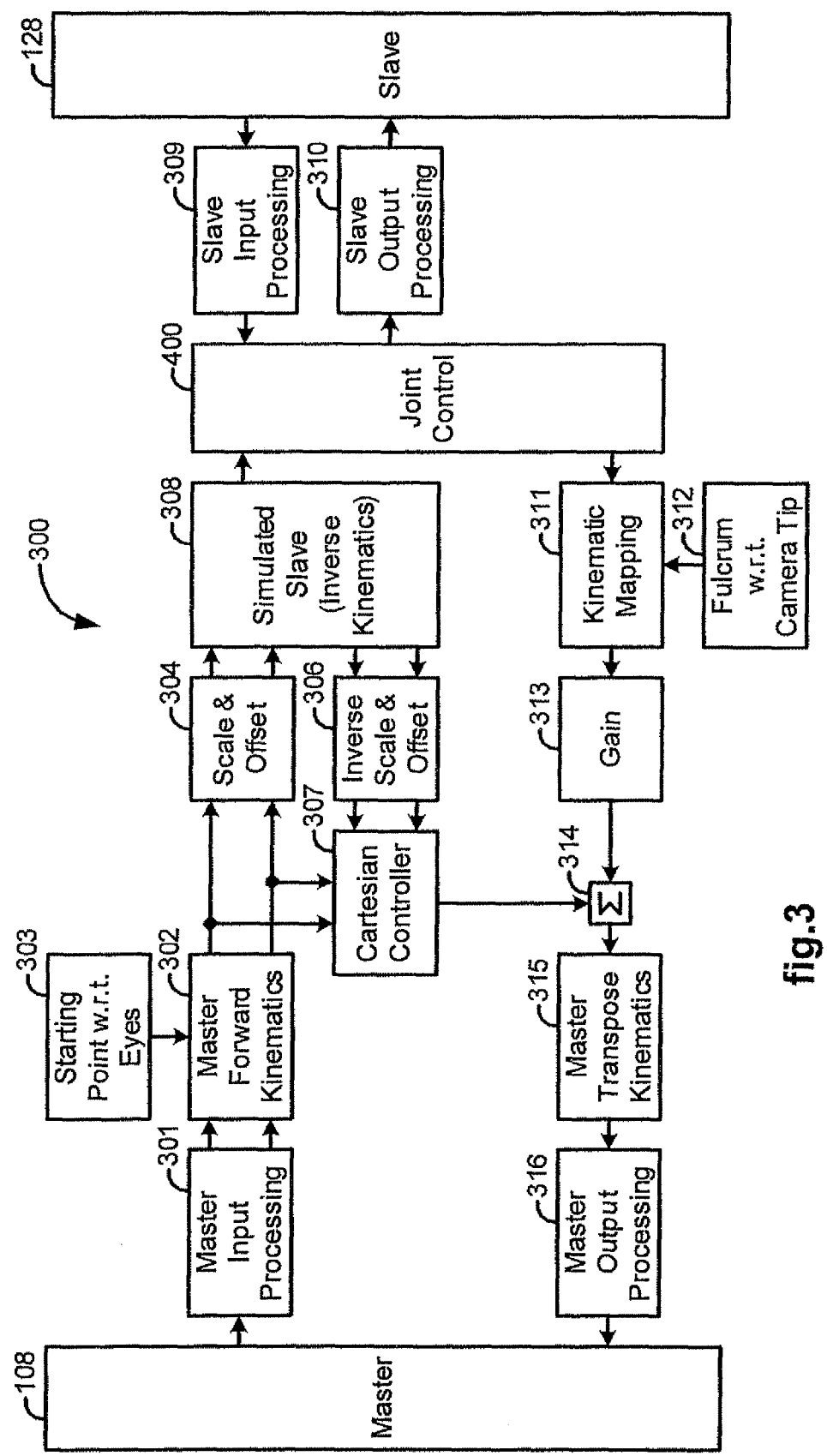
FIG. 3 illustrates a block diagram of a master/slave control system utilizing aspects of the present invention.

FIG. 3 illustrates, as an example, a block diagram of a master/slave control system 300 for controlling movement of the slave manipulator of the robotic arm assembly 128 and consequently, the position and orientation of its attached tool 138, as commanded by movement of the master manipulator 108 by a surgeon. A similar control system may also be provided for the slave manipulator of the robotic arm assembly 129 and its associated master manipulator 109.

Both the master and slave manipulators include a number of linkages connected by joints so as to facilitate multiple degrees-of-freedom movement. As the surgeon moves the master manipulator 108 from one position to another during the course of performing a surgical procedure, sensors associated with the master manipulator joints provide information indicating such command movement in master joint space, and sensors associated with the slave manipulator joints provide information indicating slave manipulator and consequently, tool 138 movement in slave joint space for feedback purposes.

A master input processing unit 301 receives the information of the master joint positions, which are sampled at the control system processing rate (e.g., 1300 Hz in the present example), from the master joint sensors in the master manipulator 108, and computes joint velocities from the sensed joint positions. A master forward kinematics processing unit 302 receives the master joint positions and velocities from the master input processing unit 301, transforms them from master joint space to corresponding positions and velocities of the master frame (i.e., the frame associated with the master manipulator 108) in Cartesian space relative to the eye reference frame (i.e., the reference frame associated with the position of the surgeon's eyes), using, for example, a Jacobian matrix and eye related information separately determined and provided in block 303.

A scale and offset processing unit 304 receives the Cartesian position and velocity commands from the master forward kinematics processing unit 302, scales the commanded movement according to a scale factor selected to perform the surgical procedure, and takes into account programmable offsets to generate desired slave tool frame (i.e., the frame associated with the tool 138) positions and velocities. The scale adjustment is useful where small movements of the slave manipulator of the robotic arm assembly 128 are desired relative to larger movement of the master manipulator 108 in order to allow more precise movement of the slave tool 138 at the surgical site. The offsets, on the other hand, determine, for example, the corresponding position and/or orientation of an end effector frame (e.g., the frame associated with an end effector of the tool 138) in the camera reference frame (i.e., the frame associated with the distal tip of the endoscope 140) relative to a position and orientation of the master frame in the eye reference frame.

A simulated slave processing unit 308 receives desired slave tool frame position and velocity commands from the scale and offset processing unit 304, and limits the desired slave tool frame position, orientation and velocities, to assigned Cartesian Limits for instance to enforce correct and intuitive operation of the tool 138 by keeping it within its dexterous workspace. The simulated slave processing unit 308 generates simulated slave joint positions and velocities corresponding to the limited slave tool frame positions and velocities, while making sure that the generated slave joint positions and velocities do not exceed the actual slave joint's range of motion and maximum velocities (i.e., joint limits) even in the vicinity of kinematic singularities for the slave kinematics.

An inverse scale and offset processing unit 306 receives the simulated joint position and velocity commands from the simulated slave processing unit 308, and performs an inverse function to that of the scale and offset processing unit 304 on them. A Cartesian controller 307 receives as first inputs, the inputs to the scale and offset processing unit 304 and as second inputs, the outputs of the inverse scale and offset processing unit 306. The Cartesian controller 307 then generates an error signal as a difference of the first and second inputs, and a Cartesian force "$F_{CART}$" from the error signal such as with the following formula:

$$F_{CART}=K(\Delta x)+B(\Delta \dot{x}) \tag{1}$$

where "K" is a spring constant, "B" is a damping constant, "$\Delta \dot{x}$" is the difference between the Cartesian velocity inputs to the Cartesian controller 307 and "$\Delta x$" is the difference between the Cartesian position inputs to the Cartesian controller 307. For an orientation error, a corresponding torque in Cartesian space is determined.

Figure 4:
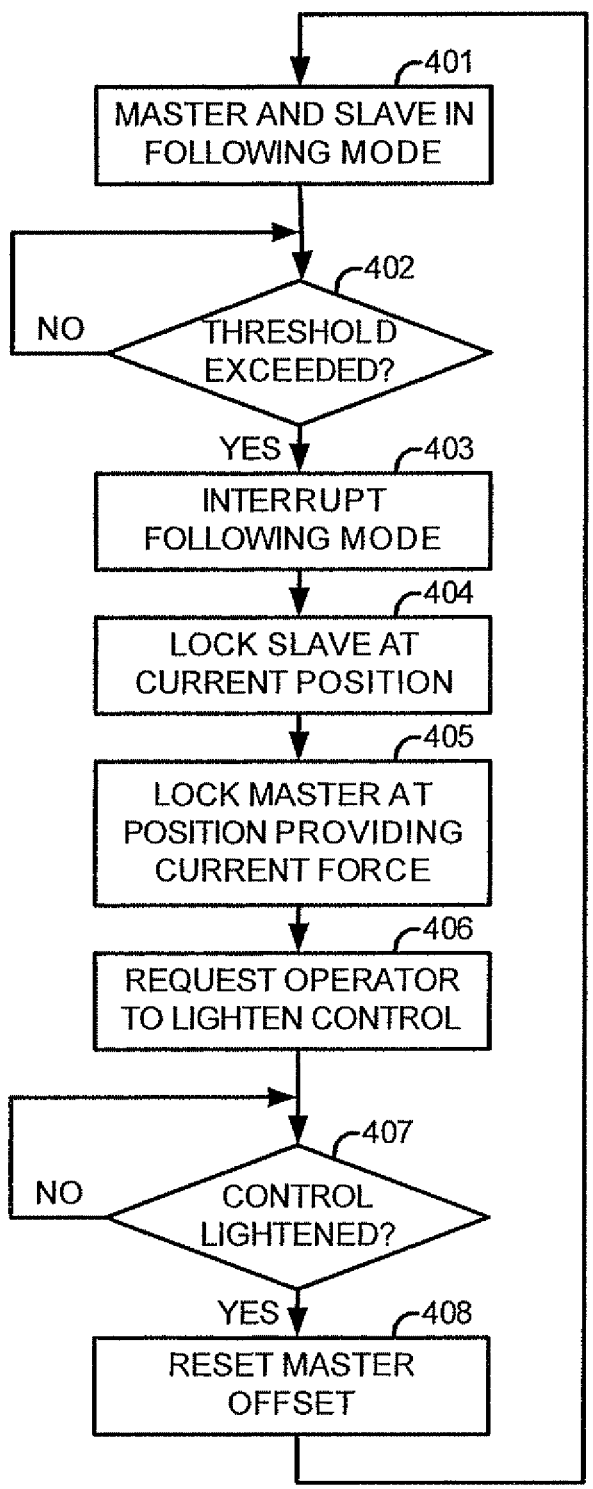
FIG. 4 illustrates a flow diagram of a method for handling an operator command exceeding a medical device state limitation in a medical robotic system, utilizing aspects of the present invention.

As will be further described in reference to FIG. 4, when the Cartesian force "$F_{CART}$" (and/or its corresponding torque in Cartesian space) exceeds a programmed threshold level, a special method for handling operator commands resulting in such force may optionally be performed for an additional level of patient safety during a minimally invasive surgical procedure.

A master transpose kinematics processing unit 315 receives the Cartesian force $F_{CART}$ through a summation node 314, and generates a corresponding torque in joint space using, for example, the Jacobian transpose matrix and kinematic relationships associated with the master manipulator 108. A master output processing unit 316 receives the master torque signals from the master transpose kinematics processing unit 315, generates electrical currents corresponding to the master torque signals, and supplies the electrical currents to corresponding master joint motors of the master manipulator 108. As a result, a surgeon operating the master manipulator 108 feels the Cartesian force, $F_{CART}$, whenever the surgeon is commanding a position or velocity which exceeds system Cartesian or slave joint limits, or would result in a kinematic singularity condition for the slave manipulator of the robotic arm assembly 128.

As the master input processing unit 301 is receiving master joint positions from sensors in the master manipulator 108, a slave input processing unit 309 is also receiving slave joint positions from position sensors in the slave manipulator at the control system processing rate. A joint control unit 400 receives the slave joint positions from the slave input processing unit 309 and the simulated joint position commands provided from the simulated slave processing unit 308, and generates slave torque command signals for the slave joint motors and master torque feedback command signals for the master joint motors.

The slave torque command signals are generated by the joint control unit 400 so as to drive joints of the slave manipulator until feedback errors calculated in the joint control unit 400 zero out. A slave output processing unit 310 receives the slave torque command signals from the joint control unit 400, converts them into appropriate electrical currents, and supplies the electrical currents to the joint motors of the slave manipulator so as to drive the motors accordingly.

The master torque feedback command signals are generated by the joint control unit 400 as a function of the slave joint position and velocity tracking errors so as to reflect forces being exerted against the tool 138 or its slave manipulator back to the master manipulator 108 so that they may be felt by the surgeon. A kinematic mapping unit 311 receives the master torque feedback command signals from the joint control unit 400, and generates the corresponding Cartesian force at the tip of the tool 138 relative to the camera frame of the endoscope 140 using the slave kinematic configuration and the previously calculated slave fulcrum (e.g., pivot point) position information provided in block 312.

A gain 313 adjusts the magnitude of the Cartesian force so as to ensure system stability while providing adequate force sensation to the surgeon. The gain adjusted Cartesian force is then passed through the summation node 314, and processed along with the Cartesian force provided by the Cartesian controller 307 through the Master transpose kinematics processing unit 315 and Master output processing 316 as previously described in reference to their processing of the Cartesian force provided by the Cartesian controller 307.

Additional details related to conventional aspects of the master/slave control system 300, such as the various reference frames referred to herein and the calculation of the surgeon eye related information provided in block 303 and the slave fulcrum information provided in block 312, which are based upon well-known mathematics, are described, for example, in the previously incorporated by reference U.S. Pat. No. 6,424,885, "Camera Referenced Control in a Minimally Invasive Surgical Apparatus."

The joint control unit 400 includes a joint controller for each active joint of the slave manipulator of the robotic arm assembly 128 that is being controlled by the master/slave control system 300. In particular, where the slave manipulator 128 includes a yaw joint 210, a pitch joint 220, and an insertion axis gear 245, such as the robotic arm assembly 200 of FIG. 2, each of these joints or gears will have its own controller.

FIG. 4 illustrates, as an example, a flow diagram of a method for handling an operator command exceeding a medical device state limitation in a medical robotic system such as the medical robotic system 100. Although the method is described herein as supplementing the haptic feedback Cartesian force "$F_{CART}$", resulting from the slave tool frame command provided to the simulated slave processing unit 308 exceeding one or more state limitations (e.g., a singularity, position or velocity limitation) as described in reference to FIG. 3 above, it may also be employed in other medical robotic systems with or without such haptic feedback. Further, although the method is described herein as responding to one or more of the state limitations described in reference to FIG. 3 being exceeded, it may also be employed in other medical robotic systems to respond to other or additional state limitations being exceeded.

In 401, the master/slave control system 300 is operating in its normal "following mode" as described above in reference to FIG. 3.

In 402, the method periodically checks to determine whether the current slave tool command would result in one or more tool state limitations being exceeded beyond programmed threshold levels. If it doesn't matter which state limitation is being exceeded and by how much, such checking may be performed in the Cartesian controller 307 by simply checking the current magnitude of the Cartesian force "$F_{CART}$". On the other hand, if it does matter which state limitation is being exceeded and/or by how much, then this task may be performed in the simulated slave processing unit 308 on each of the slave limitations for corresponding programmed threshold levels. Once it is determined in 402 that one or more state limitations is being exceeded beyond corresponding programmed threshold levels, then the method performs 403-408 as described below.

In 403, the normal "following mode" is interrupted so that the slave and master manipulators, 128 and 108, may be respectively locked in certain positions. Such interruption in this case takes the form of disengaging control of the slave manipulator 128 (and its tool 138) by the master manipulator 108.

In 404, the slave manipulator 128 is then position servoed (i.e., "locked") at its current position by, for example, switching the input to the joint control unit 400 from the output of the simulated slave processing unit 308 (as in normal "following mode" operation) to a latched value of the output of the slave input processing unit 309, so that the input to the joint control unit 400 is the same as its feedback (i.e., the output of the slave processing unit 309) at the time the 'lock' command is executed and will resist any external force tending to displace it In 405, the master manipulator 108 is position servoed (i.e., "locked") so as to maintain the current output of the Cartesian controller 307 (e.g., the Cartesian force "$F_{CART}$") being commanded on the master manipulator 108. Although shown as following 404, the order in which 404 and 405 are performed may be reversed, or preferably, they may be performed substantially concurrently.

In 406, a message is provided to the operator to lighten his or her grip on the master manipulator 108. The message may be conveyed in any conventional manner such as displaying it on a computer screen viewable to the operator, causing a pre-recorded audio message to be played on speakers (or earphones) hearable by the operator, and causing a vibration on the master manipulator 108 so as to indicate to the operator to lighten his or her hold of the master manipulator.

In 407, lightened hold of the master manipulator 108 by the operator is detected, for examples, by detecting the operator's release of a control activation button on the master manipulator 108, by a reading of a grip force sensor, or by detecting that the output of the Cartesian controller 307 has changed from $F_{CART}$ to a smaller threshold value $F_{THREAS}$ in response to a change in the readings of the master manipulator joint position sensors.

In 408, once it is determined that the operator has lightened his or her grip on the master manipulator 108, at least one parameter associated with the master manipulator 108 is set so that the slave manipulator 128 (and consequently, its tool 138) is commanded to a different state that does not exceed any of its state limitations. As an example, the programmable offset in the scale and offset processing unit 304 and its corresponding programmable offset in the inverse scale and offset processing unit 306 may be reprogrammed so that output of the Cartesian controller 307 becomes zero (from its current value that is already less than $F_{THREAS}$). After completing 408, the method then reengages control of the slave manipulator 128 by the master manipulator 108 by jumping back to 401 and reentering normal "following mode" for the master/slave control system 300.

At this time, another message may be sent to the operator so that the operator knows that control of the slave manipulator 128 may now be resumed.

Although the various aspects of the present invention have been described with respect to a preferred embodiment, it will be understood that the invention is entitled to full protection within the full scope of the appended claims.

We claim:

1. A medical system comprising:
    a medical device;
    a slave manipulator adapted to manipulate the medical device;
    a master input device operatively coupled to the slave manipulator; and
    a processor programmed to automatically determine whether the slave manipulator is being commanded by the master input device to a commanded state of the slave manipulator that is greater than or equal to a threshold value which is less than a limit of the slave manipulator; and if the slave manipulator is determined by the processor as being commanded to the commanded state that is greater than or equal to the threshold value, then the processor automatically:
    cause control of the slave manipulator by the master input device to be disengaged,
    cause the slave manipulator to remain at a current state of the slave manipulator,
    cause the master input device to remain at a current state of the master input device,
    alter a parameter that affects a functional relationship between the current state of the master input device and the commanded state of the slave manipulator so that the current state of the master input device commands a different commanded state that is not greater than or equal to the threshold value, and
    after altering the commanded state to the different commanded state, cause the control of the slave manipulator by the master input device to be re-engaged so that the different commanded state is applied to the slave manipulator.

2. The medical system according to claim 1, wherein the commanded state of the slave manipulator includes commanded positions of motor driven mechanical elements in the slave manipulator.

3. The medical system according to claim 2, wherein the commanded state of the slave manipulator further includes commanded velocities of the motor driven mechanical elements in the slave manipulator.

4. The medical system according to claim 2, wherein the motor driven mechanical elements of the slave manipulator include one or more joints.

5. The medical system according to claim 1, wherein the medical device includes a wrist mechanism for additional degrees of freedom movement beyond those provided through the slave manipulator.

6. The medical system according to claim 5, wherein the commanded state of the slave manipulator includes commanded positions of motor driven mechanical elements in the wrist mechanism.

7. The medical system according to claim 6, wherein the commanded state of the slave manipulator further includes commanded velocities of the motor driven mechanical elements in the wrist mechanism.

8. The medical system according to claim 6, wherein the motor driven mechanical elements of the wrist mechanism include one or more joints.

9. The medical system according to claim 5, wherein the commanded state of the slave manipulator includes a commanded position and a commanded orientation of the medical device in a fixed frame of reference.

10. The medical system according to claim 9, wherein the limit of the slave manipulator is a condition where the commanded position and the commanded orientation of the medical device are functions of each other.

11. The medical system according to claim 1, wherein the limit of the slave manipulator is a workspace limitation.

12. The medical system according to claim 1, wherein the limit of the slave manipulator is a limitation in a range of motion of the slave manipulator.

13. The medical system according to claim 1, wherein the limit of the slave manipulator is a condition where a singularity in movement of the slave manipulator robotically controlled medical device exists.

14. The medical system according to claim 1, wherein the processor is programmed to provide, if the slave manipulator is determined by the processor as being commanded to the commanded state that is greater than or equal to the threshold value, a message to the operator of the master input device to lighten hold of the master input device by causing the message to be displayed on a computer screen viewable by the operator.

15. The medical system according to claim 1, wherein the processor is programmed to provide, if the slave manipulator is determined by the processor as being commanded to the commanded state that is greater than or equal to the threshold value, a message to the operator of the master input device to lighten hold of the master input device by causing a pre-recorded audio message to be played on speakers hearable by the operator.

16. The medical system according to claim 1, wherein the processor is programmed to provide, if the slave manipulator is determined by the processor as being commanded to the commanded state that is greater than or equal to the threshold value, a message to the operator of the master input device to lighten hold of the master input device by causing a vibration on the master input device so as to indicate to the operator to lighten hold of the master input device.

17. The medical system according to claim 1, wherein the processor is programmed to set the at least one parameter associated with the master input device by setting the at least one parameter so that a medical device position being commanded by the master input device is the same as the current position of the medical device.

18. The medical system according to claim 17, wherein the processor is programmed to set the at least one parameter by updating an offset parameter associated with positions of the master input device and the medical device so that the medical device position being commanded by the master input device is the same as the current position of the medical device.

19. The medical system according to claim 1, wherein the processor is programmed to disengage the control of the medical device by the master input device so that the medical device remains in its current state by interrupting control of the medical device by the master input device and servoing the medical device at its current state.

20. The medical system according to claim 1, wherein the processor is further programmed to servo the master input device at a position to maintain a current feedback force on the master input device until re-engagement of the control of the medical device by the master input device, if the commanded state of the slave manipulator is greater than or equal to the threshold value.

\* \* \* \* \*